United States Patent [19]

Lackey et al.

[11] Patent Number: 5,108,396
[45] Date of Patent: Apr. 28, 1992

[54] INTRAMEDULLARY REFERENCED HUMERAL HEAD RESECTION GUIDE

[75] Inventors: Jennifer Lackey, Memphis, Tenn.; Robert Cofield, Rochester, Minn.

[73] Assignee: Smith & Nephew Richards Inc., Memphis, Tenn.

[21] Appl. No.: 534,828

[22] Filed: Jun. 7, 1990

[51] Int. Cl.⁵ .......................... A61B 17/56; A61F 5/00
[52] U.S. Cl. .......................................... 606/62; 606/87
[58] Field of Search ................. 606/86, 62, 63, 64, 606/65, 67, 79, 87, 98

[56] References Cited

U.S. PATENT DOCUMENTS

| | | | |
|---|---|---|---|
| 3,334,624 | 8/1967 | Schneider | 606/62 |
| 4,487,203 | 12/1984 | Androphy | 606/62 |
| 4,667,664 | 5/1987 | Taylor | 606/64 |
| 4,703,751 | 11/1987 | Pohl | 606/62 |
| 4,736,737 | 4/1988 | Fargie | 606/88 |
| 4,913,137 | 4/1990 | Azer | 606/64 |
| 4,952,213 | 8/1990 | Bowman | 606/62 |

Primary Examiner—Robert A. Hafer
Assistant Examiner—Michael Brown
Attorney, Agent, or Firm—Kirkpatrick & Lockhart

[57] ABSTRACT

An apparatus for guiding the resection of the head of a humerus is provided. The apparatus includes an intramedullary alignment member having a longitudinal axis and structured for substantial axial alignment with the intramedullary canal of the bone, one point of reference for the resection. The apparatus also includes an extramedullary alignment member and a collar rotatably mounted on the intramedullary member for rotating the extramedullary alignment member about the longitudinal axis of the intramedullary alignment member to a desired degree of retrotorsion. A cutting block and a first shaft and a second shaft in a perpendicular orientation relative to the first shaft for positioning the cutting block in a desired orientation relative to the head of the bone are also provided.

13 Claims, 3 Drawing Sheets

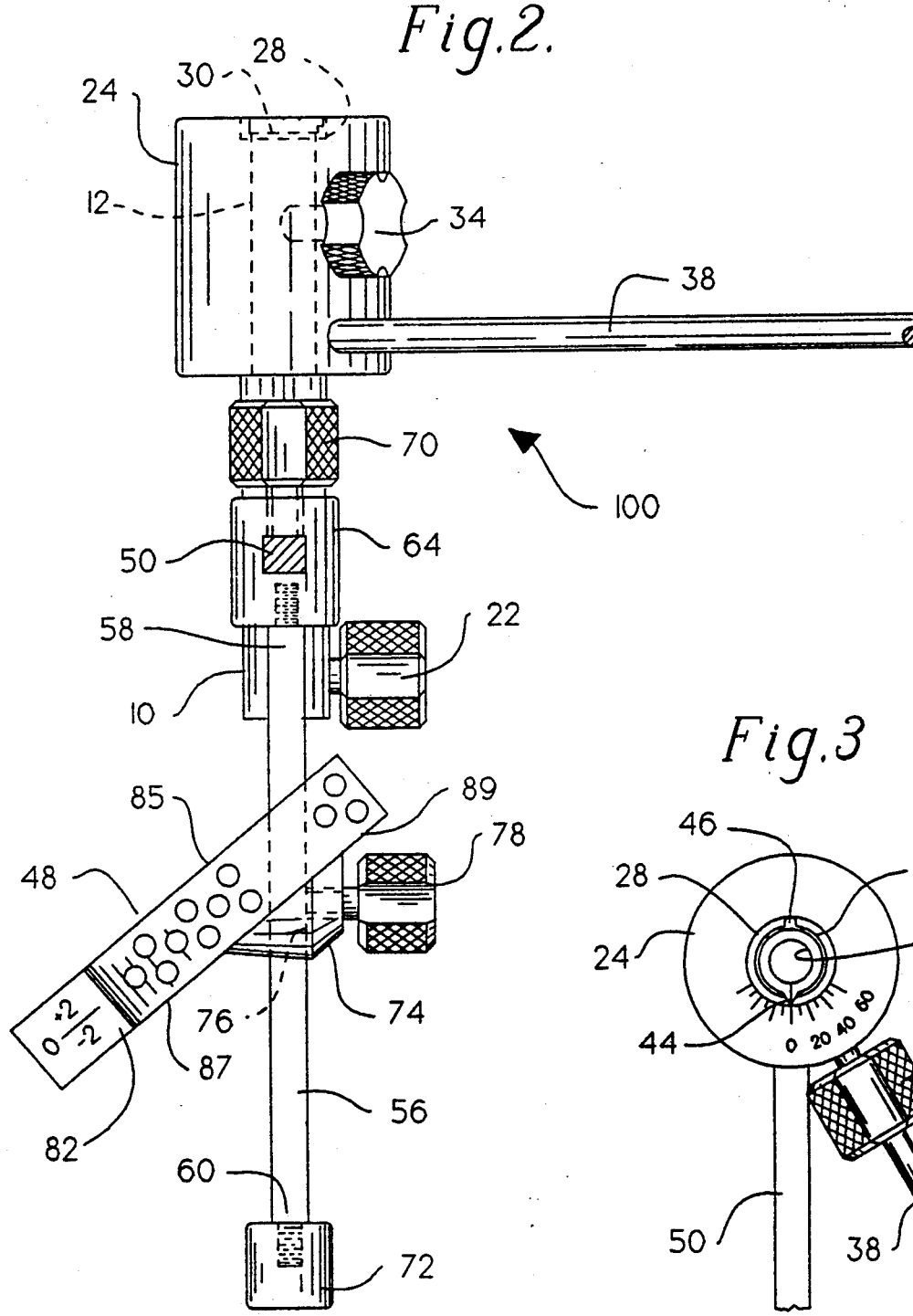

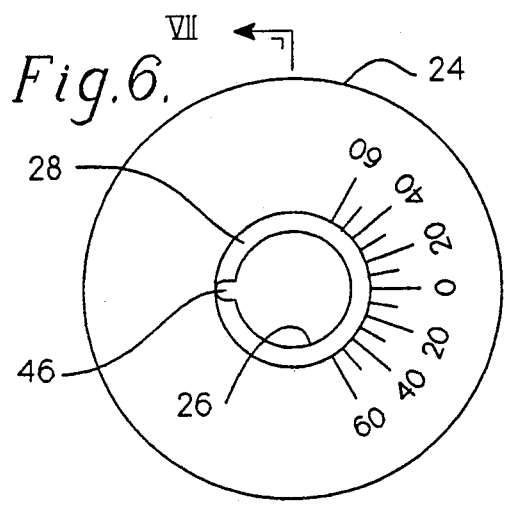
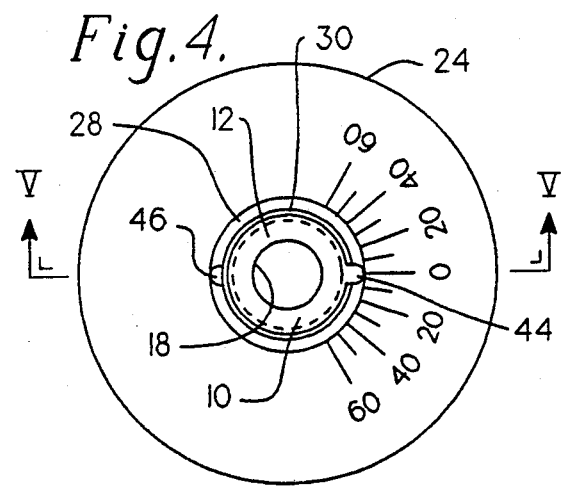
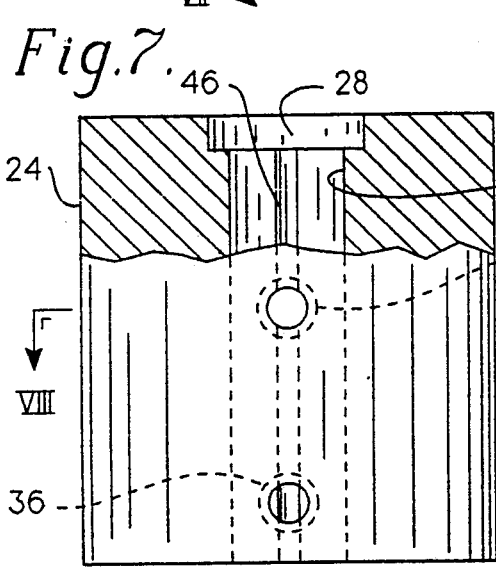
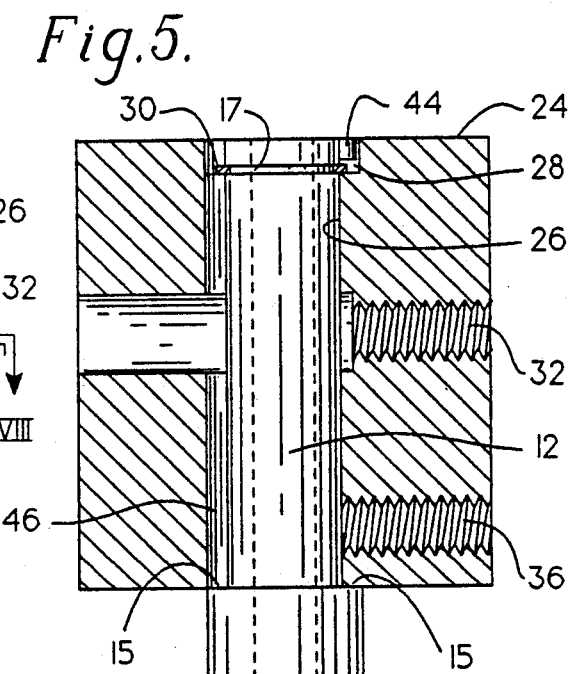
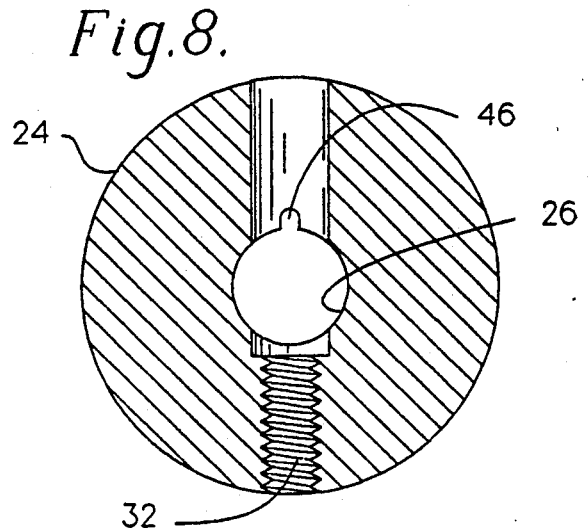
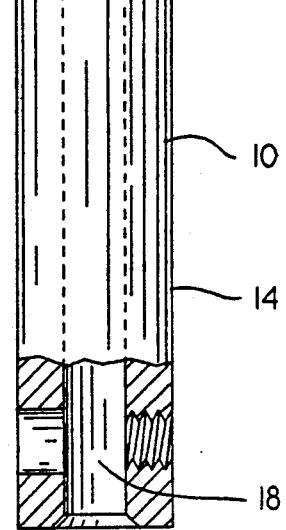

INTRAMEDULLARY REFERENCED HUMERAL HEAD RESECTION GUIDE

BACKGROUND OF THE INVENTION

1. Field of the Invention

The present invention relates to a resection guide, and more particularly to a resection guide which will ensure the correct orientation of the osteotomy cut of the head of the humerus with respect to the humeral intramedullary canal.

2. Description of the Prior Art

The humerus is the longest and largest bone of the upper limb, extending from the shoulder joint to the elbow joint where it articulates with the radius and ulna of the forearm. The proximal end of the humerus includes the humeral head which articulates with the glenoid cavity of the shoulder in a ball and socket fashion. The humeral head is nearly hemispherical in form.

As a result of certain diseases, such as rheumatoid arthritis, the humeral head may become so badly damaged that it must be resected and replaced with a prosthetic device. An acute fracture of the humeral head may also require its replacement with a prosthesis.

The prostheses typically used for this purpose include a stem portion designed to extend into the intramedullary canal of the humerus and a head portion designed to replace the humeral head. The head portion of the prosthesis extends angularly from the stem portion. The osteotomy cut of the natural humeral head must be made so that the angle of the cut corresponds to the angle between the stem and head portions of the prosthesis. In addition, the rotation of the cut varies to adjust to bone wear or capsulor looseness.

The humeral head osteotomy cut is currently being made free hand. The elbow of the patient is flexed to 90° with the patient's forearm aimed at the midline of the operating surgeon's trunk. The humerus is externally rotated 30° to 35° to provide the recommended degree of retrotorsion in relation to the axis of elbow motion. The osteotomy is directed away from the surgeon, allowing the surgeon to reproduce the desired retrotorsion in the bone cut. A trial prosthesis may also be placed along the proximal humeral shaft as a guide for the proper inclination of the osteotomy.

The possibility for error exists with this free hand or "eyeball" approach. Inaccurate resection, even by a small amount, can result in an ill-fitting prosthesis which may cause complications for the patient and may eventually require replacement of the prosthetic device. Accordingly, the need exists for a humeral cutting guide which will ensure an exact and precise resection of the humeral head.

SUMMARY OF THE INVENTION

The present invention provides an apparatus for guiding the resection of the head of the humerus. The apparatus includes an intramedullary alignment member having a longitudinal axis and being structured for substantial axial alignment with the intramedullary canal of the humerus. An extramedullary alignment member extends substantially perpendicularly from the intramedullary alignment member.

The apparatus further includes a means for rotating the extramedullary alignment member about the longitudinal axis of the intramedullary alignment member. This will allow the extramedullary alignment member to be positioned at a desired degree of retrotorsion, for example, above and substantially parallel to the forearm. The apparatus also includes a cutting block and a means for positioning the cutting block in a desired orientation relative to the head of the humerus.

In one embodiment of the present invention, the intramedullary alignment member is a rod having a proximal end and a distal end. The rod is structured for releasable attachment at the distal end to a surgical instrument temporarily disposed within the intramedullary canal. The rod may have a bore through at least a portion of it. The bore is of a diameter sufficient to receive an end of the surgical instrument. A first locking means may be provided to secure the rod to the surgical instrument.

The means for rotating the extramedullary alignment member may include a collar which is rotatably mounted on the intramedullary alignment member. The extramedullary alignment member may be threadably engaged to the collar so that rotation of the collar about the intramedullary alignment member rotates the extramedullary alignment member about the longitudinal axis of the intramedullary alignment member.

When the intramedullary alignment member is a rod having a proximal end and a distal end, the collar includes an axial bore therethrough. The bore of the collar is of a diameter sufficient to receive the proximal end of the rod. The collar preferably includes degree markings on its surface. The rod may further include a pointer at the proximal end to indicate the degree of rotation of the collar about the axis of the rod.

The means for positioning the cutting block may include a first shaft having a first end and a second end. The first end of the first shaft is attached to the intramedullary alignment member. The first shaft also has a stopping means at its second end. This stopping means may be structured to receive a second extramedullary alignment member in a coaxial relationship relative to and extending from the first shaft.

A second shaft, having a first and second ends, is also provided as part of the positioning means. The first end of the second shaft has a means for attaching the second shaft in a perpendicular orientation relative to the first shaft for slidable movement to a desired position along the first shaft. The second shaft also has a stopping means at second end. The stopping means may include an end cap threadably attached at the second end of the second shaft.

The cutting block has a boss affixed to it. A bore extends through the boss and the cutting block for receipt of the second shaft so that the cutting block is slidably movable along the second shaft. A second locking means is disposed in a transverse bore of the boss to secure the cutting block in a desired position along the second shaft.

The means for attaching the second shaft to the first shaft may include a sleeve having a bore therethrough which is capable of receiving the first shaft. A screw receiving portion is located within the sleeve and is substantially perpendicular to the bore of the sleeve. A third locking means is provided for insertion into the screw receiving portion of the sleeve.

The resection guide of the present invention may further include a means for fixing the cutting block in a desired position. The cutting block may include a plurality of holes. At least one fixation member, such as a drill, can be passed through at least one of the plurality of holes into the upper bone, near the head, thus fixing the cutting block into position.

The advantages and benefits of the present invention will become apparent from the description of the preferred embodiments hereinbelow.

BRIEF DESCRIPTION OF THE DRAWINGS

In order that the present invention may be clearly understood and readily practiced, preferred embodiments will now be described, by way of example only, with reference to the accompanying figures wherein:

FIG. 1 represents a side elevation view of the resection guide of the present invention;

FIG. 2 represents an end view of the apparatus of FIG. 1 through line II—II;

FIG. 3 represents a partial top plan view of the apparatus shown in FIG. 2;

FIG. 4 represents a top plan view of the collar and rod of FIG. 1;

FIG. 5 represents a partial section view of the rod and collar portions of the guide of FIG. 1 through line V—V of FIG. 4;

FIG. 6 represents a top plan view of the collar shown in FIG. 4;

FIG. 7 represents a partial section view of the collar portion of FIG. 6 through lines VII—VII;

FIG. 8 represents a section view of the collar shown in FIG. 7 through line VIII—VIII;

FIG. 9 represents a back elevational view of the cutting block of the present invention;

FIG. 10 represents a side elevational view of the cutting block of the present invention; and FIG. 11 represents a front elevational view of the cutting block of the present invention.

DETAILED DESCRIPTION OF THE PREFERRED EMBODIMENTS

Figures 1, 9, 10, 11:
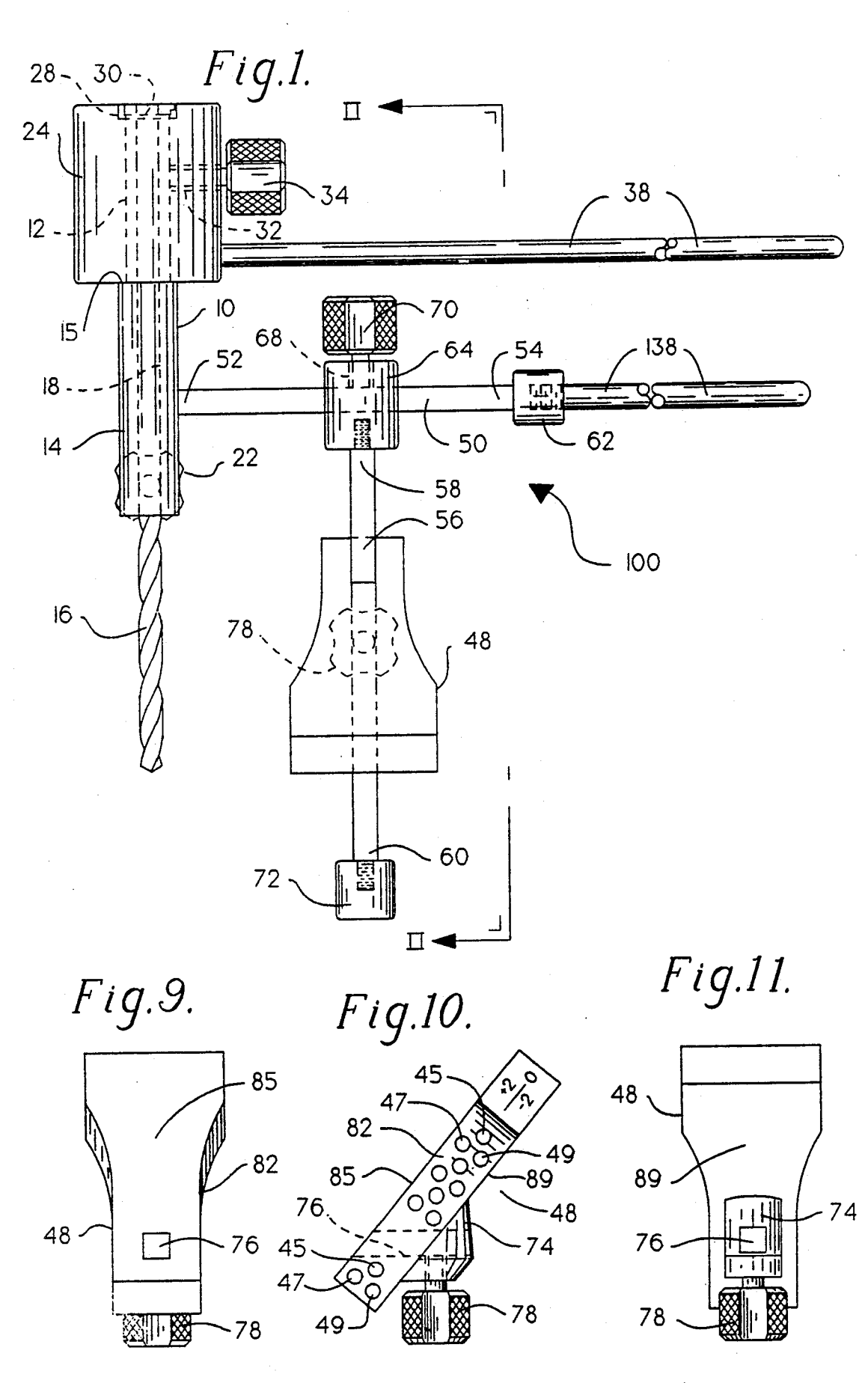

A preferred embodiment of the humeral resection guide 100 provided by the present invention is shown in FIG. 1. The guide 100 includes an intramedullary alignment member having a longitudinal axis and being structured for substantial axial alignment with the intramedullary canal of the humerus. The intramedullary canal of the humerus is one reference point for the humeral head cut.

In a preferred embodiment of the present invention, the intramedullary alignment member is a rod 10 having a proximal end 12 and a distal end 14. As shown in FIG. 5, rod 10 includes a bottom portion and a coaxial top portion. The top portion has a smaller outer dimension than that of the bottom portion. A shoulder 15 is defined at the juncture between the top and bottom portions of rod 10. A circular groove 17 is provided at proximal end 12 on the exterior of the top portion of rod 10 to receive a partially open retaining ring 30. A pointer 44 is also provided at proximal end 12 above groove 17. A longitudinal bore 18 extends through at least a portion of rod 10 along its longitudinal axis, and preferably, through its entire length as shown. Bore 18 is of a diameter sufficient to receive the shank portion of a surgical instrument such as an intramedullary drill 16 which is temporarily disposed within the intramedullary canal. The shank portion is secured to the distal end 14 of rod 10 within bore 18 by a locking screw 22.

A collar 24 is rotatably mounted on the top portion of rod 10 resting on shoulder 15. Collar 24 has an axial bore 26 into which the top portion of rod 10 is received. Collar 24 is freely rotatable about the top portion and, thus, about the longitudinal axis of rod 10.

Collar 24 also has a counterbore 28 best shown in FIGS. 4–7 Retaining ring 30 radiates outwardly from groove 17 at proximal end 12 of rod 10 and rests in counterbore 28 to secure the proximal end 12 of rod 10 within bore 26 of collar 24.

Collar 24 also has a screw receiving portion 32 positioned substantially perpendicular to rod 10 when the top portion of rod 10 is disposed within bore 26 of collar 24. A locking screw 34 is provided for insertion into screw receiving portion 32. When screw 34 is tightened, collar 24 is secured in a desired position to rod 10.

Collar 24 includes a second threaded screw receiving portion 36. Screw receiving portion 36 is also substantially perpendicular to rod 10. An extramedullary alignment member, or lateral rod, 38 as shown in FIGS. 1 and 2 is provided. One end of extramedullary alignment member 38 (not shown) is threaded for releasable attachment to collar 24 by engaging the threaded end of member 38 within screw receiving portion 36. As collar 24 is rotated about the longitudinal axis of rod 10, extramedullary alignment member 38 will also rotate about the longitudinal axis of rod 10.

This rotation will allow extramedullary alignment member 38 to provide a guide for a desired degree of humeral retrotorsion by manipulating the patient's forearm so that it is substantially parallel to extramedullary alignment member 38.

Collar 24 includes degree markings on its upper and side surfaces as shown in FIGS. 3, 4 and 6. When collar 24 is positioned over the top portion of rod 10 and pointer 44 is positioned within counterbore 28 of collar 24, pointer 44 may be used to indicate the exact and desired degree of rotation of collar 24 about rod 10. Collar 24 is turned, or rotated, to align the desired degree indicator to the pointer 44. The extramedullary rod 38, as described above, rotates about the axis of rod 10 to the same degree as indicated by the markings on collar 24. It will be appreciated that this degree of rotation corresponds to the degree of humeral retrotorsion relative to the humeral intramedullary canal. To aid in the assembly of pointer 44 within counterbore 28, bore 26 of collar 24 has a longitudinal groove 46 cut into its circumference. Groove 46 is dimensioned to be of a size and shape to complement the configuration of pointer 44. Upon passage of proximal end 12 of rod 10 through bore 26 of collar 24, pointer 44 passes through groove 46 of bore 26 to reach counterbore 28. Collar 24 is then rotated to a desired degree, as indicated by pointer 44, about rod 10.

A humeral cutting block 48, best shown in FIGS. 9-11, provides the cutting surface for a saw or cutting instrument used to resect the humeral head. Cutting block 48 must be positioned in a desired orientation relative to the humeral head. The desired angle is that which corresponds to the angle between the stem and head portions of the prosthesis. A typical orientation for the cutting surface may be at a 50° angle. However, this orientation will vary according to the type of prosthesis being used and/or the size of the patient.

A positioning means for cutting block 48 includes a first shaft 50, having a first end 52 and a second end 54, and a second shaft 56, having a first end 58 and a second end 60.

First shaft 50 is permanently attached, preferably by welding, to rod 10 and is in line with pointer 44 at first end 52. A stopping means, consisting of a sleeve 62, is placed over second end 54 of first shaft 50. Sleeve 62 may be either permanently fixed or removably attached to first shaft 50. Sleeve 62 is structured to optionally receive a second extramedullary alignment rod 138. If used, the second extramedullary alignment rod would be in a coaxial relationship relative to first shaft 50 in an end to end alignment, held in position by sleeve 62.

In certain instances, it may be desirable for the surgeon to add a second extramedullary alignment member 138, or medial rod, to sleeve 62. The second extramedullary member 138 will be in line with the osteotomy cut. If the first shaft 50 is considered to be of sufficient length to act as the medial alignment means, the second, medial, extramedullary alignment member 138, or rod, may not be necessary.

Second shaft 56 is perpendicularly attached at its first end 58 to the first shaft 50 so that second shaft 56 is slidably movable along the length of first shaft 50. A sleeve 64 is attached to second shaft 56 at first end 58. Sleeve 64 has a transverse bore therethrough to receive shaft 50. A screw receiving portion 68 is located within sleeve 64 substantially perpendicular to the transverse bore. A locking screw 70 is received in portion 68. Upon tightening of screw 70, second shaft 56 is firmly secured in a desired position along first shaft 50. When screw 70 is loosened, second shaft 56 may be moved along the length of first shaft 50 to a desired position. The second end 60 of second shaft 56 is threaded and is capable of receiving an end cap 72. End cap 72 will keep humeral cutting block 48, further described hereinbelow, from falling off of second shaft 56. First and second shafts 50 and 56, respectively, are preferably square in cross section.

Humeral cutting block 48 has a cutting surface 85 and an attachment surface 82, shown in FIG. 10. Cutting block 48 also includes a boss 74 affixed to and extending outwardly from surface 89. A bore 76, preferably square in cross section, extends through cutting block 48 and boss 74. Bore 76 is configured to receive second shaft 56 of the positioning means so that humeral cutting block 48 is slidably movable along the length of second shaft 56. Rotation about second shaft 56, however, is prevented. One hundred and eighty degree turns, however, are possible to ensure a proper cutting angle from both the left and the right side. A transverse bore is provided in boss 74 to receive a locking screw 78 so that humeral cutting block 48 may be secured in the desired position along second shaft 56 when locking screw 78 is tightened.

Humeral cutting block 48 has a plurality of holes located on attachment surface 82 of block 48. These holes, as shown in FIG. 10, are preferably arranged in three rows 45, 47 and 49. As shown, surface 82 has markings 0, +2 and −2 corresponding to each of the three rows with 0 being the middle row of holes 45. The upper and lower rows of holes 47 and 49, respectively, designated +2 and −2 respectively, are spaced two millimeters above and below the middle row of holes 45. While a variation of plus or minus two millimeters is shown, any other suitable variation will suffice.

When the cutting block is properly positioned on the positioning means, at least one fixation member, such as a drill or pin (not shown) is inserted through at least one of the plurality of holes 45 into the upper humerus. While any of the plurality of holes may be selected, it is preferable to insert the drill in at least one of the holes in the middle line 45 (0 line) of the three rows.

When only one fixation member is used, the humeral resection guide must be left in place during the resection. The guide itself will provide a second point of fixation which is necessary to obtain a steady cutting surface. Alternatively, if it is desired to remove the guide during the resection, at least two fixation members must be used to provide the cutting surface.

Upon placement of the drills or pins through at least two of the holes of cutting block 48 into the upper humerus, the entire humeral resection guide 100 may be removed. As the guide is removed, the cutting block 48 remains fixed to the upper humerus of the patient. The cutting block 48 may be removed from the drills or pins, and adjusted two millimeters higher or lower by placing the drills into either the upper (+2 line) or lower (−2 line) holes in surface 82 of cutting block 48.

In use, the surgeon makes the desired incision to expose the humeral head. Using a saw or an osteotome, a sliver of subchondral bone and any remaining cartilage is removed from the superior-lateral aspect of the humeral head. Typically, this piece is about three millimeters in thickness and two centimeters in diameter. A drill is guided through the cancellous bone of the proximal humerus into the intramedullary canal. With the drill in place, the humeral intramedullary resection guide 100 of the present invention is then position to provide a guide for precisely resecting the humeral head.

The bottom portion of rod 10 of the intramedullary alignment member is positioned over the shank of the drill 16. Locking screw 22 is tightened. Collar 24 and with it, extramedullary alignment member 38, are rotated to the desired degree of retrotorsion using the degree markings on collar 24 and pointer 44. The articular surface of the humerus is retrotorted approximately 30 to 35 degrees in relation to the axis of elbow motion. A similar retrotorsion should be recreated during this procedure. Thus, the extramedullary alignment member 38 is positioned at about the 30 to 35 degree mark on collar 24 relative to the pointer 44 on the top portion of rod 10. Locking screw 34 is then tightened to hold the collar 24 and extramedullary alignment member 38 in place relative to rod 10, thereby fixing the direction of the bone cut. The patient's forearm should be substantially parallel to the extramedullary alignment member 38.

The cutting block 48 is then moved toward the humerus and positioned by sliding second shaft 56 along first shaft 50 and cutting block 48 along second shaft 56 until the cutting block 48 is in the desired position. Locking screws 70 and 78 are tightened to fix the cutting block 48 into position on guide 100. Cutting block 48 is then fixed to the upper humerus by inserting two approximately one-eighth inch drills or pins through two holes 45 on cutting block 48 and into the upper humerus. As described above, one drill or pin may be used if the guide is left in place during resection. If the guide is to be removed during resection, at least two drills or pins must be used. Cutting block 48 is then released from second shaft 56 by loosening locking screw 78 and end cap 72. The remainder of guide 100 is removed from drill 16 by loosening locking screw 22. Drill 16 is removed from the intramedullary canal of the humerus.

Following removal of guide 100, cutting block 48 can be removed from the two drills or pins in the upper humerus and repositioned upwards or downwards by 2 millimeters to adjust the height of the cut. The cut is made using a reciprocating saw which is guided by the cutting surface 85 of cutting block 48.

After removal of the cutting block 48 and drills, the remaining peripheral osteophytes and the remaining humeral head around the anterior, medial and posterior aspects are trimmed so that the osteotomy area approximates the size of the undersurface of the head portion of the prosthesis. The intramedullary canal is then reamed to the desired degree to permit insertion of the stem portion of the prosthesis. The prosthesis is then inserted in the usual accepted manner.

While the present invention has been described in connection with preferred embodiments, it will be understood that modifications and variations apparent to those of ordinary skill in the art are within the scope of the present invention.

What is claimed is:

1. An apparatus for guiding the resection of the head of a humerus comprising:
    an intramedullary alignment member having a longitudinal axis and being structured for substantial axial alignment with the intramedullary canal of a humerus;
    an extramedullary alignment member, extending substantially perpendicularly from said intramedullary alignment member;
    means for rotating said extramedullary alignment member about the longitudinal axis of said intramedullary alignment member to be positioned at a desired degree of retrotorsion;
    a cutting block; and
    means mounted on said intramedullary alignment member from which said cutting block is operatively supported for positioning thereof in an orientation relative to the head of the humerus within a range desirable for humeral resection.

2. An apparatus as recited in claim 1 wherein said intramedullary alignment member comprises a rod having a proximal end and a distal end, said rod being structured for releasable attachment at said distal end to a surgical instrument temporarily disposed within the intramedullary canal.

3. An apparatus as recited in claim 2 wherein said rod has a bore through at least a portion thereof, said bore being of a diameter sufficient to receive an end of the surgical instrument.

4. An apparatus as recited in claim 3 further comprising first locking means to secure said rod to the surgical instrument.

5. An apparatus as recited in claim 1 wherein said means for rotating said extramedullary alignment member comprises a collar rotatably mounted on said intramedullary alignment member.

6. An apparatus as recited in claim 5 wherein said extramedullary alignment member is threadably engaged to said collar.

7. An apparatus as recited in claim 5 wherein said intramedullary alignment member comprises a rod having a proximal end and a distal end and said collar has an axial bore therethrough of a diameter sufficient to receive said proximal end of said rod.

8. An apparatus as recited in claim 7 wherein:
    said collar further comprises degree markings on a surface thereof; and
    said rod further comprises a pointer at said proximal end to indicate the degree of rotation of said collar about the longitudinal axis of said rod.

9. An apparatus as recited in claim 1 wherein said means for positioning said cutting block comprises:
    a first shaft, having a first end and a second end, and being permanently attached at said first end of said first shaft to said intramedullary alignment member and having a stopping means at said second end of said first shaft;
    a second shaft, having a first end and a second end, said first end of said second shaft having a means for attaching said second shaft in a perpendicular orientation relative to said first shaft for slidable movement to a desired position along said first shaft and having a stopping means at said second end of said second shaft;
    said cutting block being configured for slidable movement along said second shaft; and
    second locking means to secure said cutting block in a desired position along said second shaft.

10. An apparatus as recited in claim 9 wherein said means for attaching said second shaft to said first shaft comprises a sleeve having a bore therethrough to receive said first shaft and a transverse screw receiving portion; and
    third locking means for insertion into said screw receiving portion.

11. An apparatus as recited in claim 9 wherein said stopping means on said second shaft comprises an end cap threadably attachable to said second end of said second shaft.

12. An apparatus as recited in claim 9 further comprising a second extramedullary alignment member and wherein said stopping means on said first shaft is structured to receive said second extramedullary alignment member in a coaxial relationship relative to said first shaft.

13. An apparatus as recited in claim 1 further comprising means for fixing said cutting block in said desired position relative to the bone, said fixing means comprising:
    a plurality of holes through said cutting block; and
    at least one fixation member for passage through at least one of said plurality of holes and passage into the bone.

* * * * *